Feb. 26, 1974 F. ANDREA Plant Pat. 3,498
GERANIUM PLANT
Filed April 7, 1972
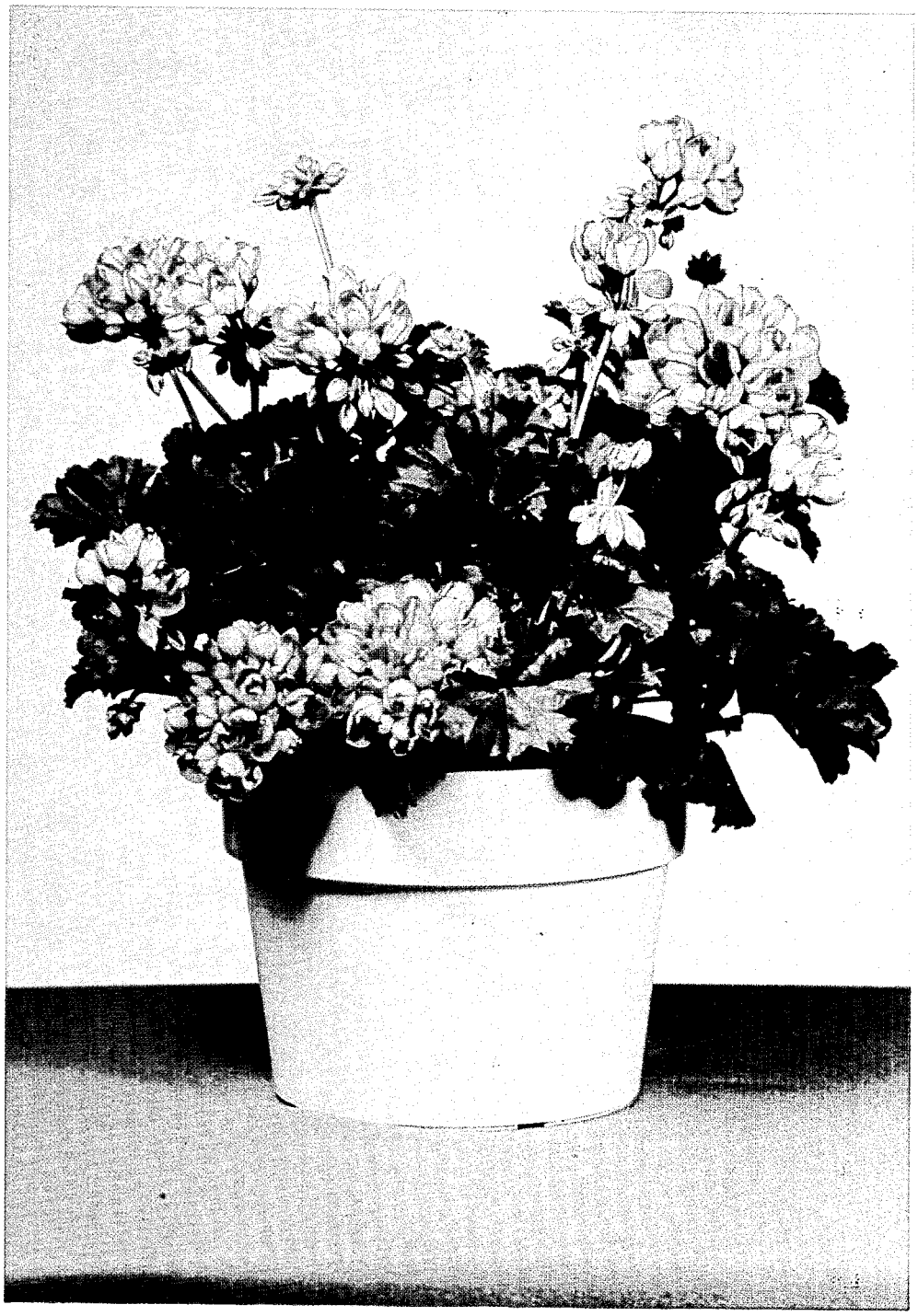

United States Patent Office

Plant Pat. 3,498
Patented Feb. 26, 1974

3,498
GERANIUM PLANT

Frank Andrea, 390 N. Franklin St.,
Holbrook, Mass. 02343

Filed Apr. 7, 1972, Ser. No. 242,147
Int. Cl. A01h *5/00*
U.S. Cl. Plt.—68 1 Claim The present discovery relates to a new and distant geranium plant. The new and patentable characteristics thereof reside in its healthy growth, its continuous and exceptionally free-blooming habits, its large and double-flowered truss, its large florets with double petalage and its distinctive color combination and unique foliage.

This geranium plant is a new and improved variety which has resulted from definite breeding programs and experiments carried on by me in my greenhouses at 390 North Franklin Street, Holbrook, Mass. My experiments covered the three year period from May 1967 to May 1970. The breeding experiments carried by me were to produce new varieties of the "Fiat" (unpatented) type. The present claimed geranium is the result of crossing the F. Andrea geranium plant patented by me Apr. 19, 1966, No. 2,621, with an unnamed seedling then crossing a seedling from the cross-breeding and back cross-breeding with the F. Andrea geranium. The claimed geranium plant is the result of one of these back cross seedlings.

The drawing shows the plant and flower of a fully developed geranium of the new variety claimed.

My new variety has the following characteristics:

THE PLANT

Growth: This new variety is a very prolific bloomer. The florets are incurved with a variable number of petals, producing a double effect. The flower "truss" head is large, and the petals last longer than usual Fiat types, giving a large display. The growth is vigorous and compact and attains an average height of 12 to 18 inches as a pot plant.

Blooming habit: Very free and continuous bloomer in winter and summer, indoors or out. A plant in a 4 inch pot produces 2 to 3 trusses at one time.

Inflorescene: Large, globular to somewhat flattened, compact umbel or truss, measuring 4–6 nches at diameter.

Foliage:

*Quantity.*—Abundant.
*Size.*—Not typical of Fiat, but large in size.
*Color.*—A dark green when well grown.
*Shape.*—Disc to cup shaped and undulate with deeply lobed edged.

*Texture.*—Firm, thick, waxy, upper surface smooth; lower surface moderately hairy with no distinct pubescence.
*Stem*: Short, strong, freely branching to produce a compact, vigorous plant.
*Peduncle*: Strong, slightly pubescent. Color slightly lighter than foliage.

THE FLOWER

Truss:

*Size.*—Large, up to 6 inches in diameter.
*Shape.*—Compact, a flattened globe as it opens.
*Number of florets.*—Variable, average is 20–25.
*Lasting quality.*—Excellent. Blooms remain open 10 days to 2 weeks, longer if kept dry. Doubleness and waxy petals resist petal rot.

Bud:

*Size.*—Approximately 1 inch in diameter.
*Color.*—Signal Red 43A (The Royal Horticultural Society Horticultural Color Chart).
*Form.*—Pointed.

Florets:

*Size.*—Approximately 1 inch in diameter.
*Petalage.*—Double, variable with 5–12 average.
*Color.*—Outer petal 43C scarlet 19/1 (The Royal Horticultural Society Horticultural Color Chart); interior petal 43B Scarlet 19 (The Royal Horticultural Society Horticultural Color Chart). Color very stable with age and does not fade.
*Texture.*—Very firm, waxy and glistening.
*Form.*—Petals are slightly serrated on the edge and overlap. When all the florets are open, the globular truss resimbled a hydrangea.
*Lasting quality.*—Average floret lasts a week and the truss up to 10 days to 2 weeks.
*Behavior.*—The petals give a distinctly double appearance to the flower and make the plant give a distinctly double appearance with a prolific habit.

Having thus disclosed my invention, I claim:

1. A new and distinct variety of geranium plant, substantially as shown and described, characterized particularly by its health growth; its continuous and exceptionally free blooming habits; its large and double flowered truss; its large florets with double petalage and distinctive red color combination.

No references cited.

ROBERT E. BAGWILL, Primary Examiner